United States Patent [19]
Hadhanyi

[11] 3,953,423
[45] Apr. 27, 1976

[54] PREPARATION OF A NEW FLAVANONE DERIVATIVE

[75] Inventor: Andreas Hadhanyi, Eschweiler-Bergrath, Germany

[73] Assignee: H. Trommsdorff, Aachen, Germany

[22] Filed: Dec. 5, 1973

[21] Appl. No.: 422,055

[30] Foreign Application Priority Data
Dec. 8, 1972 Germany............................ 2260214

[52] U.S. Cl. ............................. 260/210 F; 424/180
[51] Int. Cl.² ..................... C07G 3/00; C07H 17/04; C08B 37/00
[58] Field of Search .......... 260/345.2, 210 R, 210 F

[56] References Cited
UNITED STATES PATENTS

| | | | |
|---|---|---|---|
| 2,350,804 | 6/1944 | Ohta ................... | 260/345.2 |
| 2,744,920 | 5/1956 | Kurth ................... | 260/345.2 |
| 2,781,336 | 2/1957 | Zenczak ............... | 260/345.2 |
| 2,870,165 | 1/1959 | Hergert ................ | 260/345.2 |

OTHER PUBLICATIONS
Voss et al., Ber., 70, 122 (1937).
Murav'ev et al., Chem. Abstract, 70, 29108x (1969).

*Primary Examiner*—James O. Thomas, Jr.
*Assistant Examiner*—Nicky Chan
*Attorney, Agent, or Firm*—Burgess, Dinklage & Sprung

[57] ABSTRACT

The invention relates to a flavanone derivative of the formula $C_{29}H_{32}O_{17}$, believed to have the structure

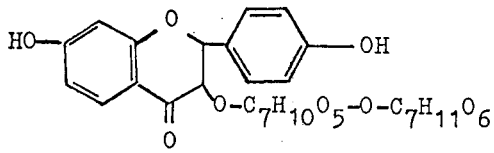

as well as its non-toxic salts. The new compound is suited for treatment of ulcers.

5 Claims, No Drawings

PREPARATION OF A NEW FLAVANONE DERIVATIVE

The present invention relates the the preparation of a new flavanone derivative.

The licorice extract, succus liquiritiae, was formerly widely recommended for ulcer-therapy. However, it became evident that the healing of ulcers was associated with water retention which led to the formation of oedema of the face and limbs, in particular the knuckles. This was sometimes accompanined by dizziness and headache. These phenomena rapidly disappeared upon the discontinuance of the administration of the medicament.

In seeking the active ingredient in succus liquiritiae, there was found glycyrrhinzinic acid. While there are now innumerable derivatives and salts of these two acids, the efficient therapeutic effect achieved with licorice juice cannot be attributed to any one of them alone.

Numerous dyestuffs must be removed when preparing chemically pure glycyrrhinzinic acid and its ammonium salt from extracts of succus liquiritiae. A commercial ammonium glycyrrhizinate of dark-brown quality is chemically very impure since it contains about 35–42% of other ingredients, particularly dyestuffs and resins. Unitl now, these substances have not been studied on a large scale nor prepared, which has to be ascribed to the fact that some of them, in particular flavones and flavanoids, are oxidized on contact with atmospheric oxygen and are immediately converted into a resin-like material.

It is accordingly an object of the present invention to prepare from available materials a new material exhibiting activity in the treatment of ulcers, which material can be utilized without the undesirable side effects which accompanied treatment with other therapeutics.

These and other objects are realized in accordance with the present invention pursuant to which there is prepared from succus liquiritiae or from commercial ammonium glycyrrhizinate a new flavanone derivative of the empirical formula $C_{29}H_{32}O_{17}$ and of probable structural formula

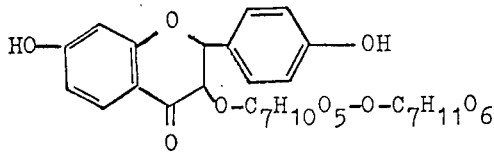

The structure of the claimed material has been established with respect to the 4',7-dihydroxyflavanone-2,3 arrangement as well as the dimeric methylated hexuronic acid esterified therewith. Only the position of the dimeric acid radical at the flavanone structure could not be unequivocally determined.

The material of the invention is prepared from a mixture obtained from licorice extract, preferably from commercial extracts of succus liquiritiae or from commercial dyestuff-containing ammoniacal glycyrrhizine. To this end, an aqueous dispersion is prepared from the starting material and is combined with ethyl urethane, thereby dissolving the undesired red dyestuff, a moderately acidic pH value is produced by adding water or diluted acid whereby glycyrrhizinic acid contaminated with yellow dyestuff precipitates, the supernatant solution containing the red dyestuff is discarded, the precipitate is dissolved in dilute alcoholic acid and is subjected to alcoholysis with simultaneous alkylation, the precipitated glycyrrhetinic acid is discarded, the supernatant solution is boiled down and the so-obtained product is dried.

The process of the invention may be modified by dissolving the commercial ammoniacal glycyrrhizine utilized as starting material in concentrated nitric acid and subsequently reacting with ethyl urethane. Other selective dissolving intermediaries known to the skilled artisan may be used in place of ethyl urethane.

The product obtained according to the process of the invention can be further purified by extracting it with a suitable solvent, such as acetone, ether, or chloroform, discarding the insoluble component, removing the solvent and drying the resulting residue. If desired, the so-obtained flavanone derivative may be further purified prior to the extraction with an organic solvent by repeated treatment with dilute methanolic hydrochloric acid and subsequent removal of any residual glycyrrhetinic acid by passage through a column filled with a polyamide ion-exchange resin.

The purification by means of an organic solvent such as acetone, ether, or chloroform may also be carried out in an earlier process step. For example, the precipitate, which is obtained after adjustment to a moderately acidic pH value and consists primarily of glycyrrhizinic acid contaminated with yellow dyestuff, may be extracted with the organic solvent.

The sequence of the process of the invention can also be modified at another stage. In any case, one should take care that undesired dyestuff and particularly the glycyrrhetinic acid are removed as completely as possible.

If ammoniacal glycyrrhizine which is dissolved in nitric acid is utilized as starting material, additional heating will not be necessary. However, if an extract of succus liquiritiae which is added to water is used as starting material, gentle heating, for example at temperatures of about 40°–95°C, preferably in the range of about 40°–80°C, is effected with constant stirring. The addition of ethyl urethane is effected in amounts of about 2 to 20%, by weight, preferably about 2 to 10%, relative to the extract used as starting material. In order completely to dissolve the undesired red dyestuff, the reaction mixture is stirred under the influence of heat for about 1 6 hours, preferably about 2 to 4 hours. The reaction time naturally depends on the temperature employed. The reaction mixture may also be allowed to stand overnight at room temperature. In order to produce a moderately acidic pH value, water is added to the so-obtained dark colored solution if the starting material has been dissolved in concentrated nitric acid. However, if the starting material has been dissolved in water, diluted acid is added to the dark colored solution in order to precipitate the glycyrrhizinic acid contaiminated with yellow dyestuff. Suitable acids are inorganic and organic acids such as hydrochloric acid, sulfuric acid, nitric acid, oxalic acid, etc. The concentration of the acid is not critical but, in general, concentrations on the order of 0.2 to 5% are utilized. Preferred acid concentrations are about 1 to 1.5%.

After the precipitate has been filtered and the filtrate discarded, the precipitate is added to a mixture of an organic solvent which is miscible with water and dilute acid. Alcohols, such as methanol and ethanol, are preferred as water-miscible solvents. As acids, the same acids as mentioned above for the precipitation may be used, the concentrations of the acids being in similar ranges as specified above. However, if it is desired to conduct the alcoholysis and the alkylation in one single process step, a dilute methanolic acid solution, particularly diluted methanolic hydrochloric acid, is preferably used.

The so-obtained solution is then heated for several hours at elevated temperature. For example, heat can be supplied for 13 hours at the reflux temperature of the reaction mixture or heating may be carried out for 3 hours in an autoclave at 130°C. The heating duration depends on the temperature utilized. The reaction mixture is cooled after heating, insoluble substances, primarily glycyrrhetinic acid, are filtered off and the filtrate may be boiled down in vacuum. The flavanone derivative according to the invention is obtained in this manner but it is still contaminated with a further yellow dye. It can be extracted with an appropriate organic solvent, such as acetone, ether or chloroform and the organic extracts are combined. After distilling off the solvent, the flavanone derivative of the invention is generally obtained in very pure form. If the so-obtained product is still contaminated with non-hydrolyzed glycyrrhizinic acid, it can be dissolved anew in methanol and dilute mineral acids and heated at reflux for several hours. The remaining glycyrrhetinic acid is then precipitated and the product of the invention exhibiting maximum purity can be extracted from this solution.

If ammonium glycyrrhizinate is used as starting material, it is dissolved in concentrated nitric acid, the dispersion is poured into a substantially larger quantity of water and combined with ethyl urethane. The still impure flavanone derivative is precipitated together with the glycyrrhizinic acid while further undesired dyestuff remains in solution and is discarded. Owing to the capability of ethyl urethane to act as dissolving intermediary, only a few dyes as well as the desired flavanone derivative remain insoluble in water. The further process steps for separating additional undesired dyestuff as well as the glycyrrhetinic acid correspond to the above-described process. However, for complete alcoholysis and simultaneous methylation, it is sufficient that one heats for 4 hours at reflux. Thereafter, the entire cleaved glycyrrhetinic acid is precipitated while the very pure flavanone derivative remains in solution. The glycyrrhetinic acid is filtered off and the filtrate is boiled down and subsequently dried.

A thin-layer chromatogram of the flavanone derivative of the invention on silica gel (silica gel sheet marketed by the Merck Company under the number 5553/0025) in a 2:1.5 water (saturated with chloroform): glacial acetic acid system shows an Rf value of 0.79. After drying the plate at 120°C, the flavanone derivative can be readily recognized due to its yellow color. If the thin-layer chromatogram is sprayed with an alkaline solution of lead salt (Deutsches Arzneibuch-Reagenz 93) the spot becomes fluorescence-quenching at 254 nm. A very weak spot appears at an Rf value of 0.54 which originates from a hitherto non-separable accompanying substance.

In spectrophotometric tests the flavanone compound of the invention shows a maximum at 245 nm. The melting point of the flavanone derivative of the invention is 240°±10°C.

No compounds could be identified in the starting material, in succus liquiritiae and in ammoniacal glycyrrhizine, which exhibited an Rf value of 0.74 in thin-layer chromatographic tests. This observation confirms that the flavanone derivative according to the invention is formed in the course of the novel process and is not present as such in the starting material.

As follows from the chromatographic analysis, the new flavanone derivative has a purity of at least 98%. It contains foreign substances which mainly consist of a yellow dyestuff of heretofore unknown constitution. These foreign substances probably stabilize the flavanone derivative of the invention, since when attempting to remove the same, the stability of the flavanone suffers.

The invention will be further described in the following illustrative examples wherein all parts are by weight unless otherwise expressed.

EXAMPLE 1

200 g of a purified extract of succus liquiritiae, which contains about 10 – 80% crude glycyrrhizine, are added to 2.5 l deionized $H_2O$ and heated to 60°C while gently stirring. A turbid solution is formed which is reacted with 10 g of ethyl urethane and allowed to stand for 2 hours in a water bath while constantly stirring. Thereafter, a 1.5 per cent sulfuric acid solution is added, thereby precipitating glycyrrhizinic acid contaminated with dyestuff from the very dark viscous solution which has formed. The supernatant liquid has a light-yellow color.

After centrifugation, the precipitate is washed nearly acid-free with water and dried, yielding 126 g of precipitate.

126 g of the precipitate are dissolved in a mixture of methanol and 1 per cent hydrochloric acid and the solution is heated for 4 hours at 130°C in an autoclave. After cooling, the precipitated alcoholysis product, the crude glycyrrhetinic acid, is removed by suction filtration. The cleaved residual sugar and the dyestuff remain in solution. Filtration follows and the filtrate is boiled down in vacuum and dried, leaving a residue of 55 g.

The residue is finely ground in a mortar incrementally with 700 ml of acetone and the acetone-soluble dyestuff component is separated from the insoluble residue by decantation. The undissolved residue is subsequently extracted with an additional 300 ml of acetone. The acetone-insoluble extract is discarded. After the acetone extracts have been combined and filtered, the acetone is distilled off. 21 g of a very dark red-brown viscous syrup are obtained as residue.

The residue is added to water and de-acidified with a strongly basic ion-exchanger in the $Cl^-$ form (Lewatit, registered trade mark of Bayer AG) and ether is added drop by drop until a formed precipitate only just dissolves. After distilling off the solvent, the resulting viscous syrup crystallizes after storing for several days. The crystals are recrystallized twice from methanol. The crystals are then extracted with chloroform, the chloroform-insoluble component is discarded, the extract is boiled down and dried. 17 g of fine dark-red crystal needles are obtained which melt at about 240±30°C with simultaneous charring.

Solubility:
  Water 22°C: slightly soluble
  Boiling water: partly soluble
  Boiling ethanol: partly soluble, better than in boiling water, no clouding
pH value:
  Water 22°C: saturated pH 4.0
  Ethanol 22°C: saturated pH 5.0

EXAMPLE 2

Example 1 is repeated except that the starting material is 200 g of commercial dyestuff-containing ammonium glycyrrhizinate (Merck, Article No. 4203).

The resulting first precipitate is not heated in methanol/hydrochloric acid but in ethanol/hydrochloric acid for 12 hours at reflux. The syrup extracted with acetone in accordance with Example 1 is dissolved in 500 ml of 4 per cent methanolic hydrochloric acid and stored for 30 hours in a dry chamber at 40°C. Deacidification and purification are carried out in the same manner as in Example 1. 65 g of the new flavanone derivative are obtained.

EXAMPLE 3

50 g of ammoniacal glycyrrhizine (Merck, Article No. 4203) are placed in a 5 l three-necked flask provided with a stirrer and subsequently reacted with 300 ml of concentrated nitric acid. The stirrer is turned on; at the same time air is blown through the three-necked flask so that the yellow nitrous gases can be blown off and the resulting foam formation controlled.

The reaction is exothermic, the temperature rising to 120°C and dropping after about 30 minutes. When yellow nitrous gases no longer escape, 1000 ml of water having 50 g of ethyl urethane dissolved therein are added very slowly. A light-yellow precipitate is formed; the precipitation is intensified by adding a further 1500 ml of water. The stirring is continued for another 30 minutes.

The precipitate is placed in a 10 l beaker with 2000 ml of water and additional 3 l of water are added. After the precipitate has settled, it is sucked off, washed as acid-free as possible and dried.

The dried precipitate is placed in an extraction thimble and completely extracted with chloroform or simply heated at reflux with chloroform. While the residue left in the extraction thimble is discarded, the chloroform extract is boiled down and the residue added to 200 ml of 5 per cent methanolic hydrochloric acid and heated for about 4 hours with a reflux condenser, thus being hydrolyzed. Upon termination of the hydrolysis, the solvent is evaporated to a final volume of about 50 ml. The remaining solution is poured into 2000 ml of cold distilled water, a fine yellow precipitate being formed. It is filtered off, washed with water and dried at about 50°C. The melting point is 240°±10°C. The thin-layer chromatographic values and the spectrophotometric values correspond to the values recited hereinabove.

The flavanone derivative is a pharmacologically interesting compound. It is particularly suitable for treating various diseases of the gastric and intestinal tract, wound cicatrization and for the treatment of inflammations. It may be applied orally or intramuscularly, in the form of dragees, pills, capsules, solutions and suppositories and also in the form of ointments or tinctures.

The new flavanone derivative is distinguished over prior art substances of the same type of activity by the absence of any side effects when taken in therapeutic dosage.

It is known, for example, that when administering succus liquiritiae and glycyrrhizinic acid water retention occurs and as a consequence thereof oedema are formed in the face and at the limbs, particularly the knuckles. In addition, the potassium level in the blood falls off upon administration of these substances which has a disadvantageous effect on the myocard and this effect is accompanied by an increase in venous pressure and a substantial increase in blood pressure. Thus, individuals who take licorice extracts are liable to suffer inter alia from heart asthma.

The glycyrrhetinic acid derivative carbenoxolone is also produced from succus liquiritiae. Carbenoxolone, generally known under the commercial name biogastrone, is the only preparation from the group of gastrotherapeutic agents for which, after very thorough studies, activity in treating stomach and duodenal ulcers and gastritis has been proven. However, this positive action is impaired by considerable side effects in 30% of the treated cases. These are mineralocorticoidal side effects which lead to an undesired retention of sodium and a likewise undesired loss of potassium if they attack the kidneys. Sodium retention is followed by retention of equivalent amounts of water resulting in an increase in blood pressure and augmented heart stress. This may give rise to hypertonia; it may result in weakening of the heart or failure of a pre-existing weakened heart. It may negatively influence an already existent tendency towards oedema. On the other hand, considerable disturbances of all functions of the body may occur due to continuous loss of potassium, in particular an abatement of the elasticity of the heart muscles.

In contrast, the new flavanone derivative is not only excellent in respect of its therapeutic activity, but, at the same time, does not exhibit any of the side effects which are typical of carbenoxolone. Therefore, while possessing nearly the same ulcer effectiveness as carbenoxolone, it is substantially more suitable for therapeutic purposes than any of the known preparations for the stomach. Detrimental effects in connection with kidneys and liver, particularly in case of diseases of the liver, do not occur after treatment with the new flavanone derivative. It has a slightly hypotensive effect and promotes the peripheral blood circulation. Likewise, it has no effect on the normal course of pregnancy and does not lead to deformities of the descendants. The new flavanone derivative was thoroughly examined in respect of its pharmacological effect, and it was compared with glycyrrhizinic acid solution and aqueous extract from succus liquiritiae. The following effects were found:

a. The granuloma growth in the case of rats resulting from implanted cotton-pellets is inhibited twice as much as with the known substances, thus giving evidence of an efficient antiinflammatory action.

b. The inhibition of local inflammatory irritations in the case of rats caused by Pyrexal[(R)], a lipopolysaccharide of salmonella abortus equi, was stronger than in the case of the known substances.

c. In the Carrageenin oedema test, the new compound shows about a fourfold stronger effect than glycyrrhizinic acid.

d. The spasmolytic action of the new substance tested according to R. Magnus in vitro with guinea pig colon was nine times better than succus liquiritiae.

e. Stomach ulcers were produced by tying up Wista rats. The new flavanone derivative showed superior ulcer inhibiting action over the comparative substances.

f. In tests for studying the formation of stress ulcers mechanically provoked by impairing the membrane of the portio glandular. gastr. it was found that the scarring was substantially improved by the claimed substance over the known substances.

h. The water retention was studied by means of diuresis tests with rats by comparing with other known diuretics. The new flavanone derivative acts diuretically with elimination of $Na^+$ and $K^+$ ions in physiological ratio.

The active material may be administered in the same dosage that succus liquiritiae has heretofore been administered, e.g. for a person weighing 70 kg a dosage of about 50–300 mg of active material 3 times a day.

If in the preparation of the novel material there are employed as alkylating agents other lower alkanols in place of methanol these will be obtained homologous derivatives of generally similar properties. The novel materials may exist as such or may be present as salts with non-toxic acids or bases, e.g. sodium or potassium salts, etc.

It will be appreciated that the instant specification and examples are set forth by way of illustration and not limitation, and that various modifications and changes may be made without departing from the spirit and scope of the present invention.

What is claimed is:

1. A flavanone dimeric methylated hexuronic acid derivative of the formula

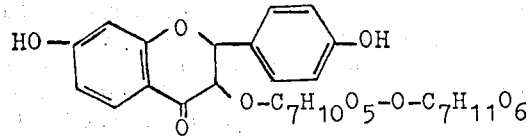

2. A method for preparing a flavanone derivative, comprising dispersing in water an extract of roots of glycyrrhiza glabra mixing the dispersion with ethyl urethane and thereby dissolving undesired red dyestuff, rendering the pH moderately acidic thereby to precipitate glycyrrhizinic acid contaminated with yellow dyestuff, separating and discarding the supernatant solution with the red dyestuff, dissolving the precipitate by means of dilute methanolic or ethanolic hydrochloric acid to cleave the sugar moiety from the glycyrrhetinic acid moiety, subjecting the sugar moiety to methylation or ethylation, and separating the precipitated glycyrrhetinic acid portion from the methylation or ethylation product which latter product contains the flavanone derivative.

3. The process of claim 2, wherein the dilute acidic lower alkanol is methanolic hydrochloric acid.

4. The process of claim 2 including the further steps of dissolving in acetone, ether or chloroform the flavanone derivative, discarding any undissolved material, and removing the acetone, ether or chloroform thereby to leave the flavanone derivative in purified form.

5. The process of claim 3, including the further steps of dissolving in acetone, ether or chloroform the flavanone derivative, discarding any undissolved material, and removing the acetone, ether or chloroform thereby to leave the flavanone derivative in purified form.

* * * * *